(12) United States Patent
Winston

(10) Patent No.: US 8,496,582 B2
(45) Date of Patent: Jul. 30, 2013

(54) APPARATUS AND METHOD FOR EXPANDING A CHEST CAVITY

(76) Inventor: Thomas R. Winston, Kansas City, MO (US)

( * ) Notice: Subject to any disclaimer, the term of this patent is extended or adjusted under 35 U.S.C. 154(b) by 1196 days.

(21) Appl. No.: 11/097,655

(22) Filed: Apr. 1, 2005

(65) Prior Publication Data

US 2006/0235278 A1 Oct. 19, 2006

(51) Int. Cl.
*A61B 1/32* (2006.01)

(52) U.S. Cl.
USPC .......................................................... 600/210

(58) Field of Classification Search
USPC .......... 606/54, 60, 72, 86, 90, 105, 205–211; 623/16.11, 23.47, 23.53; 600/201, 204, 215, 600/222, 228, 232
See application file for complete search history.

(56) References Cited

U.S. PATENT DOCUMENTS

| | | | |
|---|---|---|---|
| 4,944,753 A | 7/1990 | Burgess et al. | |
| 5,088,472 A * | 2/1992 | Fakhrai | 600/214 |
| 5,458,642 A * | 10/1995 | Beer et al. | 623/17.13 |
| 5,823,946 A | 10/1998 | Chin | |
| 5,928,231 A * | 7/1999 | Klein et al. | 606/60 |
| 5,941,819 A | 8/1999 | Chin | |
| 6,129,763 A * | 10/2000 | Chauvin et al. | 623/17.11 |
| 6,712,821 B2 | 3/2004 | Gabbay | |
| 7,306,628 B2 * | 12/2007 | Zucherman et al. | 623/17.11 |
| 2002/0072752 A1 * | 6/2002 | Zucherman et al. | 606/99 |
| 2002/0091446 A1 * | 7/2002 | Zucherman et al. | 623/17.15 |
| 2003/0083694 A1 * | 5/2003 | Miller, III | 606/216 |
| 2004/0010256 A1 * | 1/2004 | Gabbay | 606/71 |
| 2004/0225197 A1 * | 11/2004 | Roux et al. | 600/231 |
| 2005/0145510 A1 * | 7/2005 | Propp et al. | 206/208 |

* cited by examiner

*Primary Examiner* — Eduardo C Robert
*Assistant Examiner* — Tara Carter
(74) *Attorney, Agent, or Firm* — Armstrong Teasdale LLP

(57) ABSTRACT

An apparatus for expanding a chest cavity of a patient includes a tapered member and an expansion assembly coupled to the tapered member. The expansion assembly is configured to engage a sternum.

18 Claims, 5 Drawing Sheets

APPARATUS AND METHOD FOR EXPANDING A CHEST CAVITY

BACKGROUND OF THE INVENTION

This invention relates generally to surgical instruments, and more particularly, to an apparatus and method for expanding a chest cavity.

Cardiac and thoracic surgeries commonly require opening the chest through a mid-line sternotomy (the sternum is longitudinally split with a saw). Typically, after the surgery is complete, the sternum is closed by a conventional method such as stainless steel wire or a clamping mechanism. Depending on the surgery, the heart and adjacent organs may become enlarged or swell in size resulting in the exertion of greater pressure on the organs. If the pressure is left untreated, the pressure can cause post-procedure complications such as adhesions between the heart and the sternum, low-blood pressure, and arrhythmias.

At least some known methods involve implanting a sternum clamping mechanism sized to impart a predetermined space between the halves of the severed sternum. Although, the clamping mechanism may increase the space a predetermined distance, the clamping mechanisms do not allow for adjusting the space after the swelling and the pressure has increased or decreased. Additionally, some known clamping mechanism methods cause trauma to the sternum if additional access to the chest cavity is required.

BRIEF DESCRIPTION OF THE INVENTION

In one aspect, an apparatus for expanding a chest cavity of a patient is provided. The apparatus includes a tapered member and an expansion assembly coupled to the tapered member, the expansion assembly is configured to engage a sternum.

In another aspect, a sternum expansion system for a patient is provided. The system includes an implantable wedge member and a plurality of adjustable members coupled to the wedge member, the adjustable member is configured to adjustably expand a patient chest cavity.

In a further aspect, a method of expanding a chest cavity having a sternum is provided. The method includes inserting a chest cavity expander comprising a tapered member and an expansion assembly coupled to the tapered member and applying a force to the tapered member such that the sternum spreads a first distance. The method also includes adjusting the expansion assembly such that the sternum spreads a second distance greater than the first distance.

DETAILED DESCRIPTION OF THE INVENTION

Figure 1:
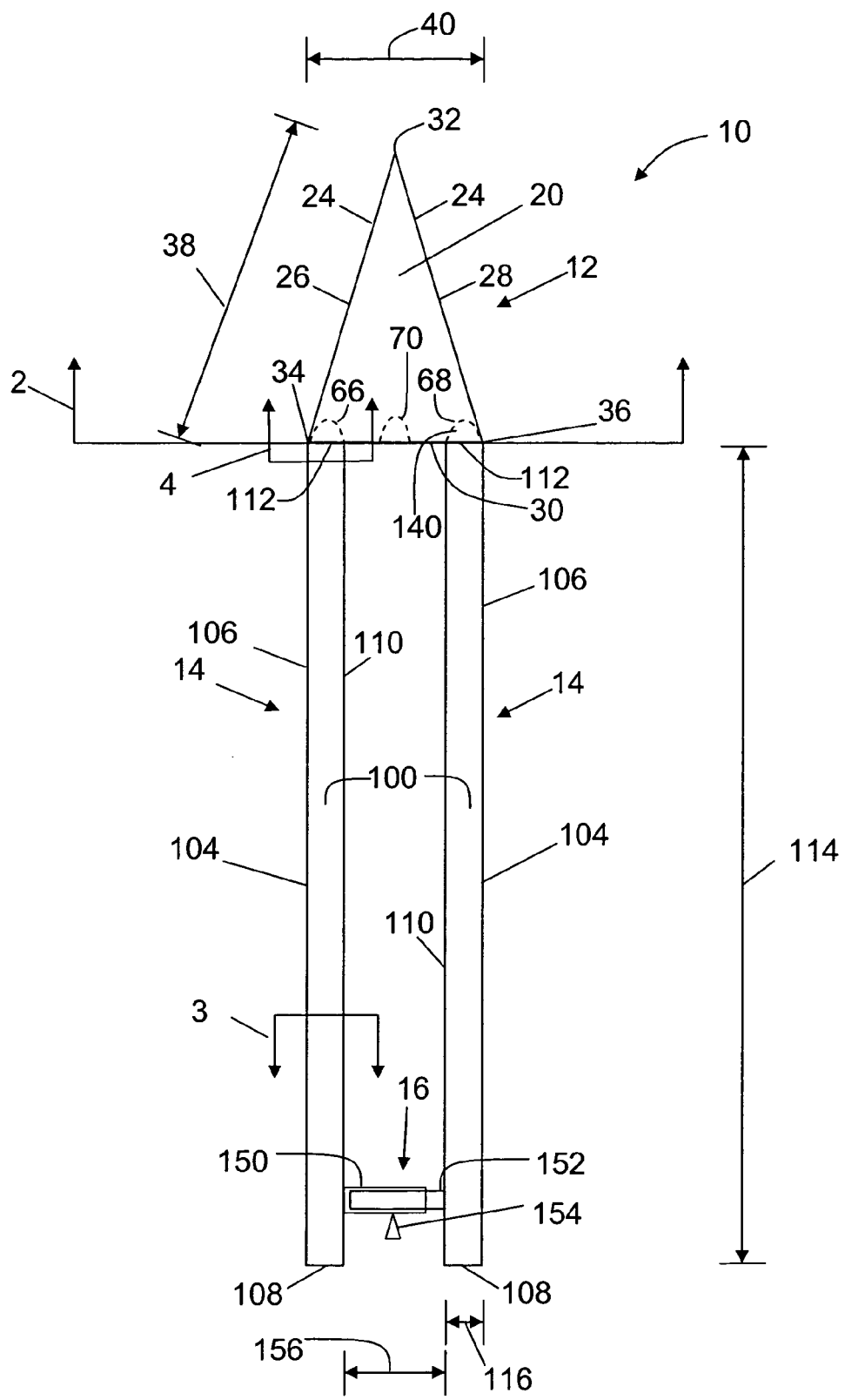
FIG. 1 is a top view of a chest expander having a tapered member and two elongate members.
Figure 2:
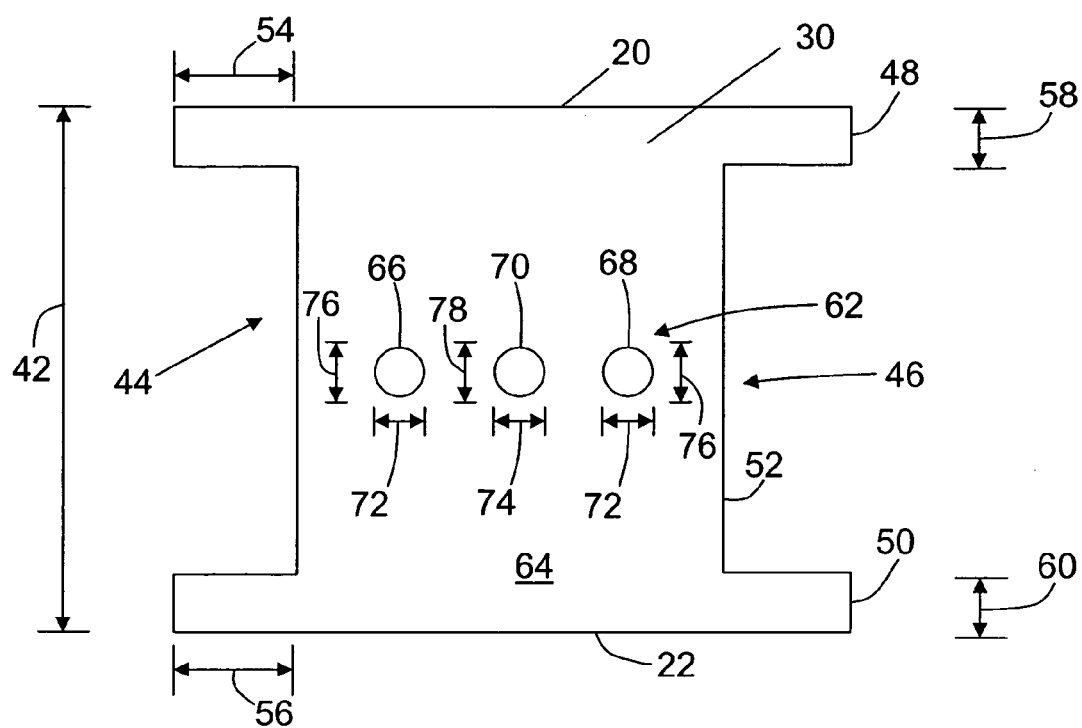
FIG. 2 is an end view of the tapered member shown in FIG. 1.

FIG. 1 is top view of a chest cavity expander 10 including a tapered member 12 coupled to a pair of elongate members 14. FIG. 2 is an end view of tapered member 12. In the exemplary embodiment, elongate members 14 are coupled to one another by an expansion assembly 16. In an alternative embodiment, elongate members 14 are not coupled to one another. Tapered member 12 and elongate members 14 may have various shapes and sizes to facilitate expanding an individual's chest cavity to a desired size and shape. In the exemplary embodiment, tapered member 12 is triangular in shape. In alternative embodiments, tapered member 12 may have another shape, such as, but not limited to a polygon shape, e.g., a pentagon shape or a hexagon shape, or a quadrilateral shape, e.g., a trapezoid shape, a rhombus shape, or a curvilinear shape. In the exemplary embodiment, tapered member 12 is fabricated from a surgical steel. In alternative embodiments, tapered member 12 is fabricated from any other suitable material that enables tapered member 12 to function as described herein, such as, but not limited to a ceramic material, a plastic material, a bone-substitute material, a titanium material, and a porous material.

In the exemplary embodiment, tapered member 12 includes an anterior surface 20, a posterior surface 22, and a plurality of sidewalls 24 extending therebetween. Specifically, in the exemplary embodiment, tapered member 12 includes a first sternum sidewall 26, a second sternum sidewall 28, and a base wall 30. First and second sternum sidewalls 26 and 28 and base wall 30 are substantially perpendicular to anterior surface 20 and posterior surface 22. First and second sternum sidewalls 26 and 28 are coupled to one another and form a leading edge 32. In the exemplary embodiment, edge 32 is straight. In an alternative embodiment, edge 32 is arcuate. In another embodiment, edge 32 is sharpened or rounded. Additionally, first and second sternum sidewalls 26 and 28 are coupled to base wall 30. As such, a second edge 34 and a third edge 36 are formed, respectively. In the exemplary embodiment, edges 32, 34, and 36 are fabricated by a molding process. Alternatively, edges 32, 34, and 36 are fabricated by other processes, such as, but not limited to, a forming process, a milling process, and a grinding process.

Sternum sidewalls 26 and 28 have a first length 38, and base wall 30 has a second length 40. In the exemplary embodiment, length 38 is different than length 40. Alternatively, lengths 38 and 40 may be selected to be any length. Additionally, sidewalls 24 have a height 42. In one embodiment, first length 38 has length proportional to second length 40 and second length 40 is between approximately 1.75 inches and approximately 2.5 inches. In another embodiment, first length 38 and second length 40 are greater than 2.5 inches. In one embodiment, height 42 is approximately 0.375 inches. In alternative embodiments, first length 38, second length 40, and/or height 42 may be longer or shorter than the above indicated lengths and heights, depending on the particular application and the size of an individual patient's sternum.

In the exemplary embodiment, sidewall 26 includes a groove 44 extending between leading edge 32 and second edge 34 and sidewall 28 includes a groove 46 extending between leading edge 32 and third edge 36. In an alternative embodiment, sidewalls 24 are substantially flat and do not include grooves 44 and 46. In the exemplary embodiment, grooves 44 and 46 are rectangular in shape. In alternative embodiments, grooves 44 and 46 may have any other shape, such as, but not limited to a polygon shape or a curvilinear shape. In the exemplary embodiment, grooves 44 and 46 are fabricated by a molding process. Alternatively, grooves 44 and 46 may be fabricated by other processes, such as, but not limited to, a forming process, a milling process, or a grinding process. Grooves 44 and 46 facilitate guiding and securing tapered member 12, for example, between a severed sternum and between a non-severed sternum, or the like.

Grooves 44 and 46 each include an anterior lip 48, a posterior lip 50, and a body 52 extending therebetween. Anterior lips 48 and posterior lips 50 are substantially parallel to one another. As such, anterior lips 48 and posterior lips 50 are substantially perpendicular to sidewalls 26 and 28, respectively. Anterior lips 48 have a length 54, and posterior lips 50 have a length 56. In the exemplary embodiment, length 54 is the same as length 56. In an alternative embodiment, length 54 is different than length 56. Alternatively, lengths 54 and 56 are selected to be any length. Additionally, anterior lips 48 have a thickness 58, and posterior lip 44 has a thickness 60. In the exemplary embodiment, thickness 58 is the same as thickness 60. In an alternative embodiment, thickness 58 is different than thickness 60. In another alternative embodiment, thicknesses 58 and 60 may be tapered. Alternatively, thicknesses 58 and 60 may be selected to be any thickness. In one embodiment, length 54 is approximately 0.375 inches and length 56 is approximately 0.375 inches. In one embodiment, thickness 58 is approximately 0.0625 inches and thickness 60 is approximately 0.0625 inches. In alternative embodiments, lengths 54 and 56, and/or thicknesses 58 and 60 may be longer or shorter than the above indicated lengths and thicknesses, depending on the particular application and the size of an individual patient's sternum.

In the exemplary embodiment, base wall 30 includes a plurality of slots 62 extending inwardly from a base surface 64. Slots 62 facilitate positioning tapered member 12 and locating elongate members 14 with respect to the patient's sternum. In the exemplary embodiment, slots 62 are co-planar. In an alternative embodiment, slots 62 are not co-planar.

In the exemplary embodiment, slots 62 are circular in shape. In alternative embodiments, slots 62 may have any other shapes, such as, but not limited to a polygon shape, a quadrilateral shape, or a curvilinear shape, such as, an oval shape. In the exemplary embodiment, slots 62 are fabricated by a molding process. Alternatively, slots 62 may be fabricated by other processes, such as, but not limited to, a forming process, a milling process, and a grinding process.

Specifically, in the exemplary embodiment, base wall 30 includes a first slot 66, a second slot 68, and a positioning slot 70 positioned therebetween. In one embodiment, slots 66, 68, and 70 are co-linear. In an alternative embodiment, slots 66, 68, and 70 are not co-linear. Slots 66 and 68 have a first diameter 72 and slot 70 has a second diameter 74. In the exemplary embodiment, diameter 72 is different than diameter 74. Alternatively, diameters 72 and 74 may be selected to be any diameter. Additionally, slots 66 and 68 have a first height 76 and slot 70 has a second height 78. In the exemplary embodiment, height 76 is different than height 78. Alternatively, lengths 76 and 78 may be selected to be any length.

First and second slots 66 and 68 facilitate providing a coupling point for elongate members 14. As such, slots 66 and 68 facilitate locating coupling members, such as elongate coupling members (not shown in FIG. 2), with respect to tapered member 12. In the exemplary embodiment, slots 66 and 68 facilitate providing a rotatable coupling. In an alternative embodiment, slots 66 and 68 facilitate providing a fixed coupling.

Slot 70 facilitates positioning tapered member 12 within the sternum. In the exemplary embodiment, slot 70 is sized to receive a surgical pin (not shown). In alternative embodiments, slot 70 is sized to receive any tool, such as, but not limited to a punch, a wedge, and a mallet. As such, when tapered member 12 is inserted between a sternum, a surgical pin may be inserted into slot 70 and a force provided by a mallet to drive tapered member 12 through the sternum and position the tapered member 12 between the two halves of the sternum. In the exemplary embodiment, tapered member 12 is secured between the two halves of the sternum by friction. In an alternative embodiment, tapered member 12 is secured between the two halves of the sternum by a fastener, such as, but not limited to a sternal wire, a natural or synthetic bone substitute material, an injectable paste, a moldable putty, and/or an adhesive material. Additionally, in another alternative embodiment, tapered member 12 is covered with a sheath (not shown) of flexible biocompatible material, such as, but not limited to an animal pericardium or a NO-REACT® tissue product (commercially available from Shelhigh, Inc. of New Jersey.)

Figure 3:
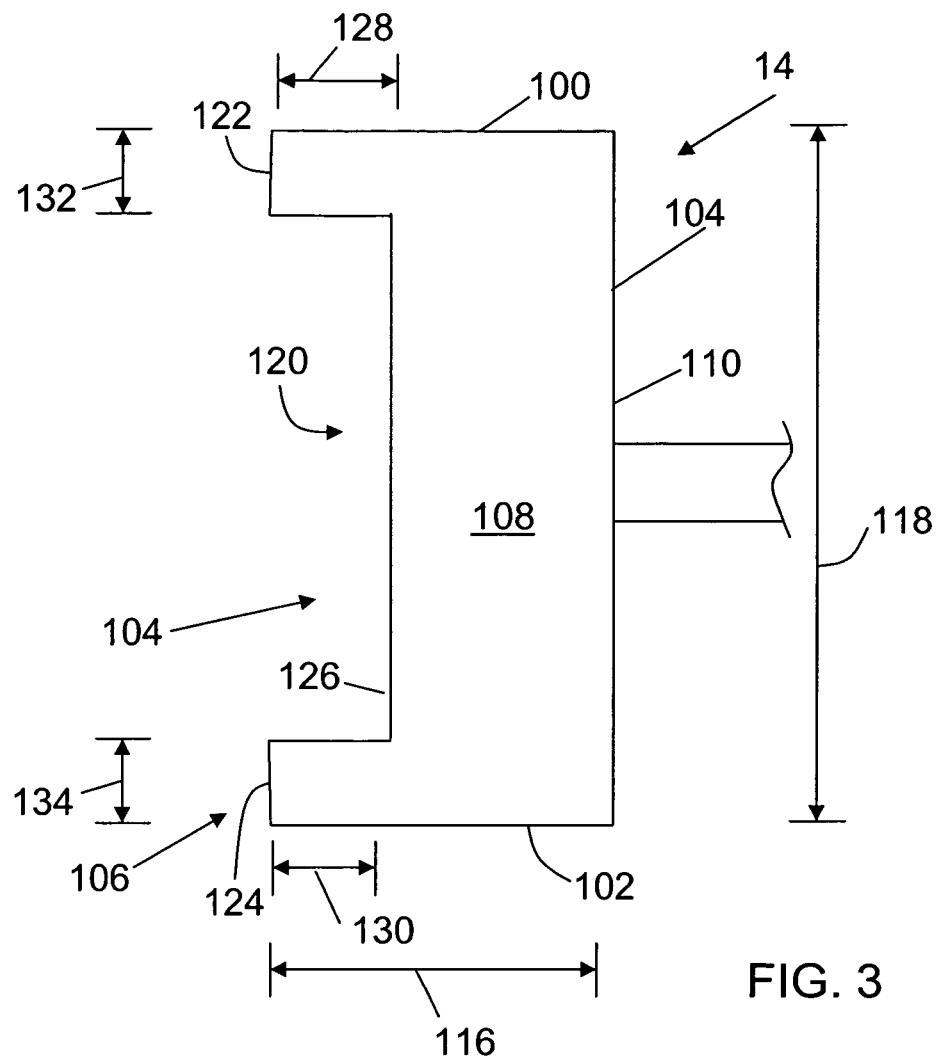
FIG. 3 is an end view of one of the elongate members shown in FIG. 1.

FIG. 3 is a side view of one elongate member 14. In the exemplary embodiment, elongate member 14 is rectangular in shape. In alternative embodiments, elongate member 14 has another shape, such as, but not limited to a polygon shape, or a curvilinear shape. In the exemplary embodiment, elongate member 14 is fabricated from a surgical steel. In alternative embodiments, elongate member 14 is fabricated from any other suitable material that enables elongate member 14 to function as described herein, such as, but not limited to a ceramic material, a plastic material, a natural or synthetic bone substitute material, a titanium material, and a porous material.

In the exemplary embodiment, each elongate member 14 includes an anterior surface 100, a posterior surface 102, and a plurality of sidewalls 104 extending therebetween. Specifically, in the exemplary embodiment, each elongate member 14 includes a first sidewall 106, a second sidewall 108, a third sidewall 110, and a fourth sidewall 112 (shown in FIG. 1). First and third sidewalls 106 and 110 are substantially parallel to one another, and second and fourth sidewalls 108 and 112 are substantially parallel to one another. As such, first and third sidewalls 106 and 110 are substantially perpendicular to second and fourth sidewalls 108 and 112. First sidewall 106 is configured to engage a portion of the sternum, third sidewall 110 is configured to engage an adjacent third sidewall 110, and fourth side wall 112 is configured to engage tapered member 12.

First and third sidewalls 106 and 110 have a first length 114, and second and fourth sidewalls 108 and 112 have a second length 116. In the exemplary embodiment, length 114 is substantially different than length 116. Alternatively, lengths 114 and 116 may be selected to be any length. Additionally, sidewalls 106, 108, 110, and 112 have a height 118. In an alternative embodiment, height 118 may be tapered. In one embodiment, first length 114 is between approximately 5.0 inches and approximately 5.125 inches, second length 116 is approximately 0.875 inches. In one embodiment, height 118 is between approximately 0.375 inches. In alternative embodiments, first length 114, second length 116, and/or height 118 may be longer or shorter than the above indicated lengths and heights, depending on the particular application and the size of an individual patient's sternum.

In the exemplary embodiment, sidewalls 106 include a groove 120 extending between sidewalls 108 and 112. In an alternative embodiment, sidewalls 106 are substantially flat and do not include groove 120. In another embodiment, sidewalls 106 include a fenestrated leading edge (not shown) configured to insert within the patient's sternum and facilitate tissue re-growth thereon.

In the exemplary embodiment, groove 120 is rectangular in shape. In alternative embodiments, groove 120 has another shape, such as, but not limited to a polygon shape, or curvilinear shape. In the exemplary embodiment, groove 120 is fabricated by a molding process. Alternatively, groove 120 may be fabricated by other processes, such as, but not limited to, a forming process, a milling process, or a grinding process.

Groove 120 facilitates guiding and securing elongate member 14, for example, between a severed sternum and between a non-severed sternum, or the like. In the exemplary embodiment, elongate member 14 is secured between the two halves of the sternum by friction. In an alternative embodiment, elongate member 14 is secured between the two halves of the sternum by a fastener, such as, but not limited to a sternal wire, a natural or synthetic bone substitute material, an injectable paste, a moldable putty, and an adhesive material. In another embodiment, sidewalls 106 include a fenestrated leading edge (not shown) configured to insert within the patient's sternum and facilitate tissue re-growth thereon. Additionally, in another alternative embodiment, tapered member 12 is covered with a sheath (not shown) of flexible biocompatible material, such as, but not limited to an animal pericardium or a NO-REACT® tissue product.

Groove 120 includes an anterior lip 122, a posterior lip 124, and a body 126 extending therebetween. Anterior lip 122 and posterior lip 124 are substantially parallel to one another. As such, anterior lip 122 and posterior lip 124 are substantially perpendicular to sidewall 106. Anterior lip 122 has a length 128, and posterior lip 124 has a length 130. In the exemplary embodiment, length 128 is the same as length 130. In an alternative embodiment, length 128 is different than length 130. Alternatively, lengths 128 and 130 may be selected to be any length. Additionally, anterior lips 122 have a thickness 132, and posterior lip 126 has a thickness 134. In the exemplary embodiment, thickness 132 is the same as thickness 134. In an alternative embodiment, thickness 132 is different than thickness 134. In another alternative embodiment, thicknesses 132 and 134 is tapered. Alternatively, thicknesses 132 and 134 are selected to be any thickness. In one embodiment, length 128 is approximately 0.375 inches and length 130 is approximately 0.375 inches. In one embodiment, thickness 132 is between approximately 0.0625 inches and thickness 134 is between approximately 0.0625 inches. In alternative embodiments, lengths 128 and 130, and/or thicknesses 132 and 134 are longer or shorter than the above indicated lengths and thicknesses, depending on the particular application and the size of an individual patient's sternum.

Figure 4:
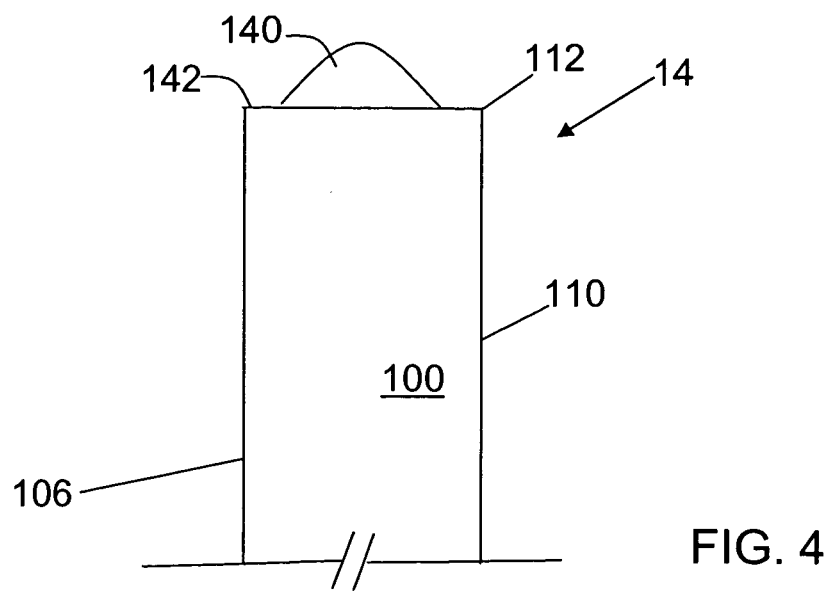
FIG. 4 is a top view of a portion of one of the elongate members shown in FIG. 1.

FIG. 4 is top view of a portion of one elongate member 14. In the exemplary embodiment, each fourth sidewall 112 includes a coupling member 140 extending outwardly from a fourth sidewall surface 142. Coupling members 140 facilitate coupling elongate members 14 to tapered member 12 (shown in FIG. 1) and positioning elongate members 14 adjacent to the patient's sternum. In the exemplary embodiment, coupling members 140 are co-planar. In an alternative embodiment, coupling members 140 are not co-planar. In another alternative embodiment, coupling members 140 extend inwardly from fourth sidewall surface 142. It is noted that the exemplary coupling members 140, as well as, slots 66 and 68, are intended for illustrative purposes only, and that the herein described chest expander 10 may be used with differently configured coupling members 140 and slots 66 and 68 than illustrated.

In the exemplary embodiment, coupling members 140 are dome shaped. In alternative embodiments, coupling members 140 have any other shape, such as, but not limited to a cylindrical shape, a cone shape, a pyramid shape, a prism, and a curvilinear shape. Alternatively, coupling members 140 are any coupling member, such as, but not limited to a hinge member, a swivel member, and a joint member, or a mechanism, such as, but not limited to a cam mechanism, a crank and slide mechanism, a linkage mechanism, and a stem and swivel mechanism. In the exemplary embodiment, couplers 140 are fabricated by a molding process. Alternatively, couplers 140 are fabricated by other processes, such as, but not limited to, a forming process, a milling process, and a grinding process.

Returning to FIG. 1, expansion assembly 16 extends between sidewalls 110. In the exemplary embodiment, at least one expansion assembly 16 extends between sidewalls 110. In an alternative embodiment, a plurality of expansion assemblies 16 extend between sidewalls 110. In the exemplary embodiment, expansion assembly 16 extends between sidewalls 110 substantially proximate sidewalls 108. In an alternative embodiment, expansion assembly 16 is positioned along elongate members 14 between sidewalls 108 and 112.

In the exemplary embodiment, expansion assembly 16 includes a first coupling member 150, a second coupling member 152, and a fastener 154 in mechanical communication with each of coupling 150 and 152. In the exemplary embodiment, coupling member 150 is sized to receive coupling member 152 therein such that elongate members 14 are spaced apart a distance 156. In an alternative embodiment, coupling members 150 and 152, are any mechanism, such as, but not limited to a ratchet-crank mechanism, a piston-housing mechanism, a fastener-slider mechanism, a cam mechanism, a crank and slide mechanism, a linkage mechanism, and a stem and swivel mechanism. In the exemplary embodiment, coupling members 150 and 152 are fabricated by a molding process. Alternatively, coupling members 150 and 152 are fabricated by other processes, such as, but not limited to, a forming process, a milling process, or a grinding process.

In the exemplary embodiment, fastener 154 is configured to adjustably couple coupling members 150 and 152 to one another. In an alternative embodiment, fastener is configured to fixedly couple coupling members 150 and 152 to one another. Fastener 154 facilitates adjusting distance 156 between elongate members 14, and as such, expands or decreases the chest cavity. In the exemplary embodiment, fastener 154 is adjusted during implantation of the chest expander 10. In an alternative embodiment, fastener 154 is adjusted in vivo, and as such, the chest cavity can be expanded or decreased in vivo. Expansion assembly 16 is configured to facilitate adjustably expanding the chest cavity volume from about 5% to about 25%.

Figure 5:
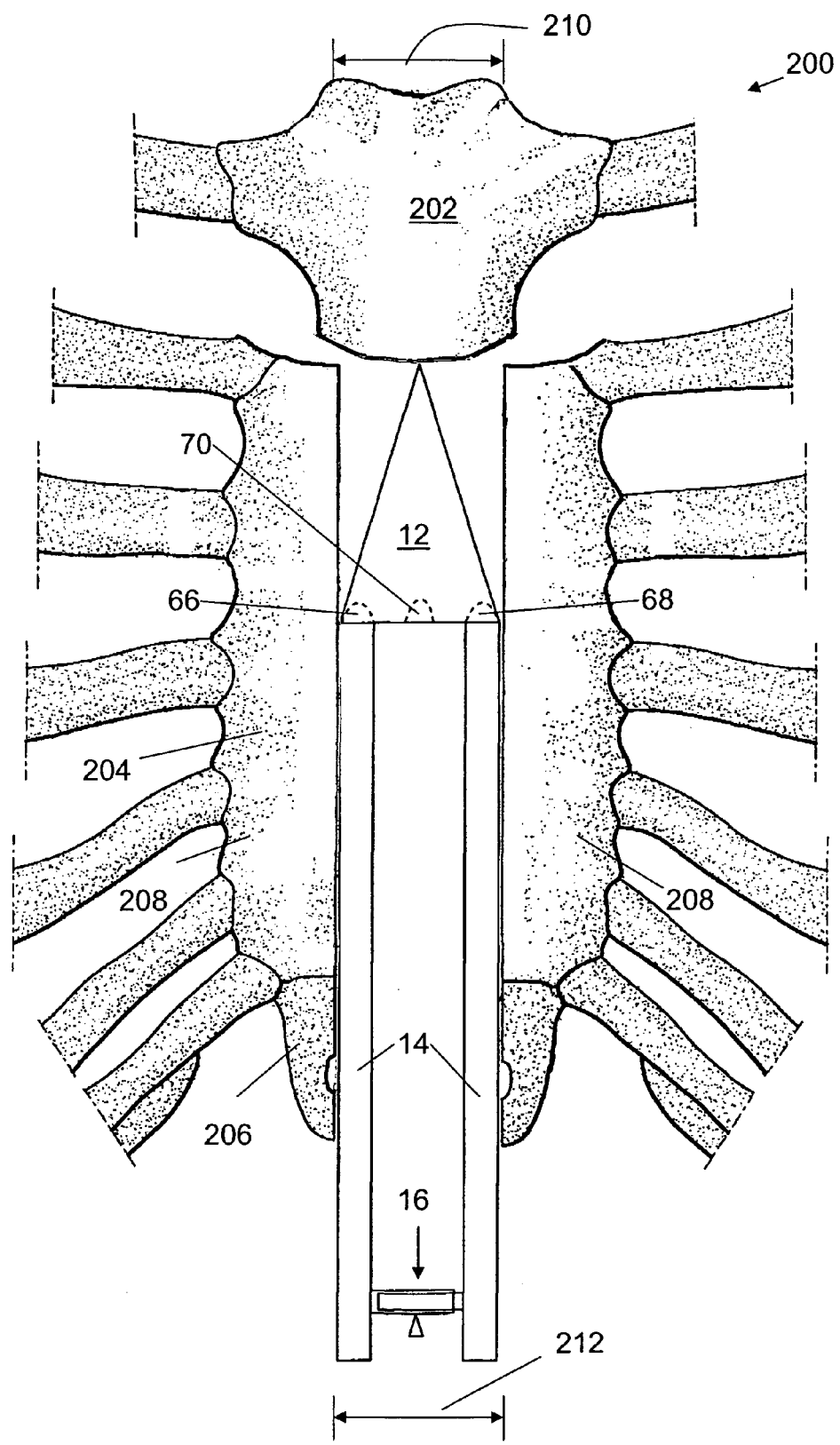
FIG. 5 is a top view of the chest expander shown in FIG. 1 in position in a sternum.
Figure 6:
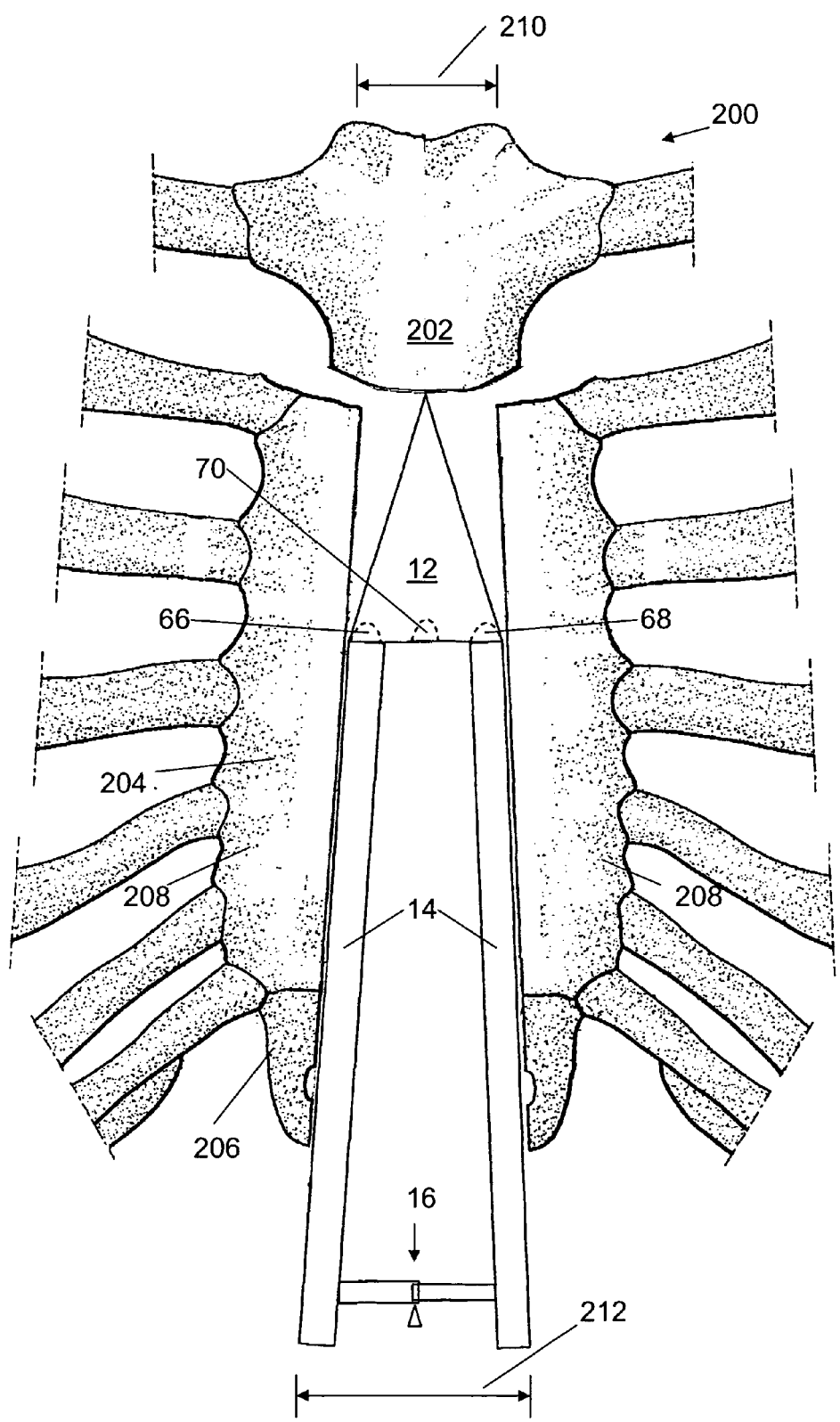
FIG. 6 is a top view of the chest expander shown in FIG. 1 in the expanded position in the sternum.

FIG. 5 is a top view of chest expander 10 positioned within a sternum 200. FIG. 6 is a top view of chest expander 10 in an expanded position in sternum 200. Sternum 200 includes a top portion or manubrium 202, a body or gladiolus 204, and a lower portion or xiphoid process 206. In the exemplary embodiment, chest expander 10 is inserted at the conclusion of cardiac or thoracic (sternotomy) surgery after sternum 200 has been severed into first and second halves 208. In an alternative embodiment, chest expander 10 facilitates severing sternum 200 into first and second halves 208.

In the exemplary embodiment, sternum 200 is severed longitudinally from xiphoid process 206 to gladiolus 204 into first and second halves 208 and severed transversely between manubrium 202 and gladiolus 204. In the exemplary embodiment, tapered member 12 is inserted and then elongate members 14 are attached thereafter. In an alternative embodiment, chest cavity expander 10 is inserted as a unit including tapered member 12 coupled to elongate members 14. Upon insertion of tapered member 12, first and second sternum halves 208 are separated and/or spread a first distance 210. In the exemplary embodiment, distance 210 is equal to base wall length 40.

In the exemplary embodiment, elongate members 14 are coupled to tapered member base slots 66 and 68 and to one another at expansion assembly 16 such that xiphoid process 206 spreads a second distance 212. As shown in FIG. 5, in one embodiment, second distance 212 is equal to first distance 210. As shown in FIG. 6, in one embodiment, second distance 212 is greater than first distance 210. Expansion assembly 16 facilitates adjusting second distance 212 either during the conclusion of surgery at wound closure, or after wound closure in vivo. In the exemplary embodiment, expansion assembly 16 facilitates adjustably increasing second distance 212 such that the chest cavity volume may be expanded from about 5% to about 25%.

In an alternative embodiment, chest expander 10 is inserted between first and second halves 208 such that sternum 200 remains separated by distance 212 until tissue re-growth is complete and covers chest expander 10 and reconnects first and second halves 208. In one embodiment, at least one of a natural or synthetic bone substitute material, an injectable paste, a moldable putty, and/or an adhesive material is inserted between chest expander 10 until tissue re-growth is complete and chest expander is removed. In another embodiment, chest expander 10 is covered with a sheath (not shown) of flexible biocompatible material, such as, but not limited to an animal pericardium or a NO-REACT® tissue product until tissue re-growth is complete. Additionally, in another alternative embodiment, a portion of the rectus abdominis muscles or a rectus abdominis free flap is harvested from the patient and re-connected such that chest expander 10 is covered and not exposed prior to tissue re-growth Additionally, chest expander 10 is removable after tissue re-growth is complete and the chest cavity has been expanded permanently.

In the above alternative embodiment, at least a centimeter or more is added to the width of sternum 200. If permanent expansion is desired, a portion of the patient's diaphragm (not shown) may be excised. In one embodiment, a triangular shaped portion is excised. In alternative embodiments, the excised portion may have any other shape, such as, but not limited to a curvilinear shape. The excised portion is replaced with a membrane or other material to accommodate the increase in chest cavity volume. In one embodiment, a Gore-Tex membrane is used. In alternative embodiments, a flexible biocompatible material is used.

It can be understood and appreciated that chest expander 10 can be provided in a variety of sizes, each having a different length, width, height, or thickness so as to approximate the length and thickness of the sternum and enable corresponding increases in the volume of the patient's chest cavity. Additionally, a variety of suitable types of rigid biocompatible materials, both natural and synthetic, can be utilized.

While the invention has been described in terms of various specific embodiments, those skilled in the art will recognize that the invention can be practiced with modification within the spirit and scope of the claims.

What is claimed is:

1. An apparatus for expanding a chest cavity of a patient, said apparatus comprising:
   an implantable tapered member; and
   an implantable expansion assembly coupled to said tapered member, said expansion assembly configured to engage a sternum, said expansion assembly comprising a first elongate member having a first end portion coupled to said tapered member and a second end portion, a second elongate member having a first end portion coupled to said tapered member and a second end portion, and an implantable expander coupled to said second end portions of said first and second elongate members and configured to move both said first and second elongate members such that said first end portions of said first and second elongate members are spaced apart a first distance, and said second end portions of said first and second elongate members are spreadable a second adjustable distance, wherein said apparatus is implantable in said chest cavity.

2. An apparatus in accordance with claim 1 wherein said tapered member is triangular-shaped and comprises:
   a first sternum side;
   a second sternum side coupled to said first side such that an edge is formed therebetween; and
   a base side coupled to said first and second sides, wherein the first distance is substantially similar to a length of said base side.

3. An apparatus in accordance with claim 2 wherein said base side includes at least one slot, said at least one slot configured to receive at least one of a mallet, a punch, and a pin to facilitate positioning said implantable tapered member within the sternum.

4. An apparatus in accordance with claim 1 wherein said first end portion of each said elongate member is coupled substantially perpendicular to said tapered member and is substantially rectangular-shaped and comprises an anterior side, a posterior side opposite said anterior side, and a pair of sternum sides extending therebetween, each said sternum side substantially concave-shaped.

5. An apparatus in accordance with claim 1 wherein said first end portion of each said elongate member is flexibly coupled to a base side of said tapered member such that said second end portion of each said elongate member is configured to orient non-perpendicularly to said base side.

6. An apparatus in accordance with claim 1 wherein said expander is at least one of a ratchet-crank mechanism, a piston-housing mechanism, and a fastener-slider mechanism, said expander configured to at least one of increase and decrease the second adjustable distance between said second end portions of said first elongate member and said second elongate member such that a volume within the chest cavity is increased between about 5% and about 25%.

7. An apparatus in accordance with claim 6 wherein said expander is configured to at least one of increase and decrease said distance in vivo.

8. A sternum expansion system for a patient, said system comprising:
   an implantable wedge member; and
   a plurality of implantable, adjustable members each having a first end portion coupled to said wedge member and a second end portion, each said adjustable member configured to move and adjustably expand a patient chest cavity such that said first end portions of said plurality of implantable, adjustable members are spaced apart a first distance, and said second end portions of said plurality of implantable, adjustable members are spreadable a second adjustable distance.

9. A system in accordance with claim 8 wherein said wedge member comprises at least one cutting edge and at least one base side, said wedge member configured to spread a first sternum portion and a second sternum portion the first distance, wherein the first distance is substantially similar to a length of said at least one base side.

10. A system in accordance with claim 9 wherein said plurality of adjustable members comprises a pair of grooved elongate members and at least one adjustable connecting member coupled therebetween, said connecting member configured to expand the first and second portions of the sternum the second adjustable distance, said second adjustable distance greater or less than said first distance, said pair of grooved elongate members facilitate guiding said plurality of adjustable members between the first and second sternum portions.

11. A system in accordance with claim 10 wherein said connecting member further comprises a locking mechanism, said locking mechanism adjustable in vivo.

12. A system in accordance with claim 8 wherein said plurality of adjustable members are configured to adjustably expand a patient chest cavity volume between about 5% and about 25%.

13. A method of expanding a chest cavity having a sternum, said method comprising:
    inserting an implantable chest cavity expander comprising a tapered member and an expansion assembly coupled to the tapered member, the expansion assembly comprising a first elongate member having a first end portion coupled to the tapered member and a second end portion, a second elongate member having a first end portion coupled to the tapered member and a second end portion;
    applying a force to the tapered member such that a first portion of the sternum spreads a first distance; and
    adjusting the expansion assembly such that a second portion of the sternum spreads a second distance greater than the first distance, the first end portions of the first and second elongate members spaced apart approximately the first distance and the second end portions of the first and second elongate members spaced apart approximately the second distance.

14. A method in accordance with claim 13 wherein said inserting an implantable chest cavity expander comprises implanting the chest cavity expander in a body portion of the sternum with at least one of a sternum wire, a bone graft, and a fastener.

15. A method in accordance with claim 13 wherein said inserting an implantable chest cavity expander comprises transversely cutting the sternum below a manubrium portion of the sternum and configuring the chest cavity expander to allow tissue growth thereon.

16. A method in accordance with claim 13 wherein said applying a force to the tapered member comprises applying a co-planer force with at least one of a mallet and a hammer.

17. A method in accordance with claim 13 wherein said adjusting the expansion assembly comprises adjusting at least the second end portions of the first and second elongate members in vivo to facilitate expanding a chest cavity volume between about 5% and about 25%.

18. A method in accordance with claim 13 wherein said inserting a chest cavity expander comprises implanting the chest cavity expander in a body portion of the sternum such that the chest cavity expander remains in the chest cavity and allows tissue growth thereon.

* * * * *